United States Patent
Su et al.

(10) Patent No.: US 11,751,061 B2
(45) Date of Patent: *Sep. 5, 2023

(54) SYSTEMS, APPARATUSES AND METHODS FOR SECURE WIRELESS PAIRING BETWEEN TWO DEVICES USING EMBEDDED OUT-OF-BAND (OOB) KEY GENERATION

(71) Applicant: Becton, Dickinson and Company, Franklin Lakes, NJ (US)

(72) Inventors: Yi Su, Acton, MA (US); Ping Zheng, Acton, MA (US); Mojtaba Kashef, Boxford, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/989,571

(22) Filed: Nov. 17, 2022

(65) Prior Publication Data

US 2023/0156475 A1     May 18, 2023

Related U.S. Application Data

(63) Continuation of application No. 16/613,033, filed as application No. PCT/US2018/033614 on May 21, 2018, now Pat. No. 11,516,673.

(Continued)

(51) Int. Cl.
*H04L 9/08*     (2006.01)
*H04W 12/50*     (2021.01)
(Continued)

(52) U.S. Cl.
CPC ........... *H04W 12/50* (2021.01); *A61B 5/0024* (2013.01); *A61M 5/14244* (2013.01);
(Continued)

(58) Field of Classification Search
CPC .. H04W 12/50; H04W 12/041; H04L 9/0838; H04L 9/0643; H04L 2209/805
See application file for complete search history.

(56) References Cited

U.S. PATENT DOCUMENTS

2009/0327724 A1   12/2009   Shah
2010/0005294 A1   1/2010   Kostiainen et al.
(Continued)

FOREIGN PATENT DOCUMENTS

EP     2 320 621 A1     5/2011
WO     2016/058965 A1     4/2016

OTHER PUBLICATIONS

Extended European Search Repot dated Apr. 24, 2020, which issued in the corresponding European Patent Application No. 18806543.7.

(Continued)

*Primary Examiner* — Ali S Abyaneh
(74) *Attorney, Agent, or Firm* — Dickinson Wright PLLC

(57) ABSTRACT

Devices, systems and methods are provided to implement key generation for secure pairing between first and second devices using embedded out-of-band (OOB) key generation and without requiring the devices to have input/output (IO) capability to enter authentication information. Bluetooth Smart or Low Energy (BLE) OOB pairing option can be used for pairing medical devices with added security of OOB key generation. The OOB key generation comprises providing first and second devices with the same predefined credential and secure hashing algorithm, and making input of the hashing algorithm of the first and second devices the same. The first device transmits unique data to second device (e.g., via BLE advertising) to share and compute a similar input. The first and second devices use the credential and shared data with the hashing function to generate a key that is the same at each of first and second devices.

13 Claims, 12 Drawing Sheets

Related U.S. Application Data

(60) Provisional application No. 62/509,383, filed on May 22, 2017.

(51) Int. Cl.
    *A61B 5/00*          (2006.01)
    *A61M 5/142*      (2006.01)
    *H04W 12/041*     (2021.01)
    *A61B 5/145*      (2006.01)
    *H04L 9/06*        (2006.01)

(52) U.S. Cl.
    CPC ......... *H04L 9/0838* (2013.01); *H04W 12/041* (2021.01); *A61B 5/14532* (2013.01); *A61B 2560/0209* (2013.01); *A61M 2205/3569* (2013.01); *A61M 2205/3584* (2013.01); *A61M 2205/505* (2013.01); *A61M 2205/8212* (2013.01); *H04L 9/0643* (2013.01); *H04L 2209/805* (2013.01); *H04L 2209/88* (2013.01)

(56) References Cited

U.S. PATENT DOCUMENTS

| | | |
|---|---|---|
| 2010/0115279 A1 | 5/2010 | Frikart et al. |
| 2010/0211685 A1 | 8/2010 | McDowall |
| 2011/0170692 A1* | 7/2011 | Konrad ................ G06F 21/606 380/260 |
| 2011/0221590 A1 | 9/2011 | Baker et al. |
| 2012/0328061 A1 | 12/2012 | Chow |
| 2013/0189924 A1 | 7/2013 | Pedro |
| 2014/0295761 A1 | 10/2014 | Lo |
| 2014/0325065 A1 | 10/2014 | Birtwhistle et al. |
| 2015/0025503 A1 | 1/2015 | Searle et al. |
| 2015/0341785 A1 | 11/2015 | Young et al. |
| 2017/0026777 A1* | 1/2017 | Denboer ........... H04W 72/0446 |
| 2017/0164192 A1 | 6/2017 | Schussmann |
| 2017/0201886 A1* | 7/2017 | Yang .................... H04W 12/06 |
| 2018/0040954 A1 | 2/2018 | Richardson |
| 2018/0352435 A1 | 12/2018 | Donley |
| 2018/0352583 A1 | 12/2018 | Smith |
| 2019/0166502 A1* | 5/2019 | Chaskar .............. H04W 12/122 |
| 2020/0162896 A1 | 5/2020 | Su |

OTHER PUBLICATIONS

Yan Michalevsky et al: "MASHaBLE: Mobile Applications of Secret Handshakes over Bluetooth LE", Mobile Computing and Networking, ACM, 2 Penn Plaza, Suite 701, New York 10121-0701, USA, Oct. 3, 2016, pp. 387-400.

International Search Report dated Aug. 24, 2018, which issued in corresponding PCT Patent Application No. PCT/US2018/033614.

* cited by examiner

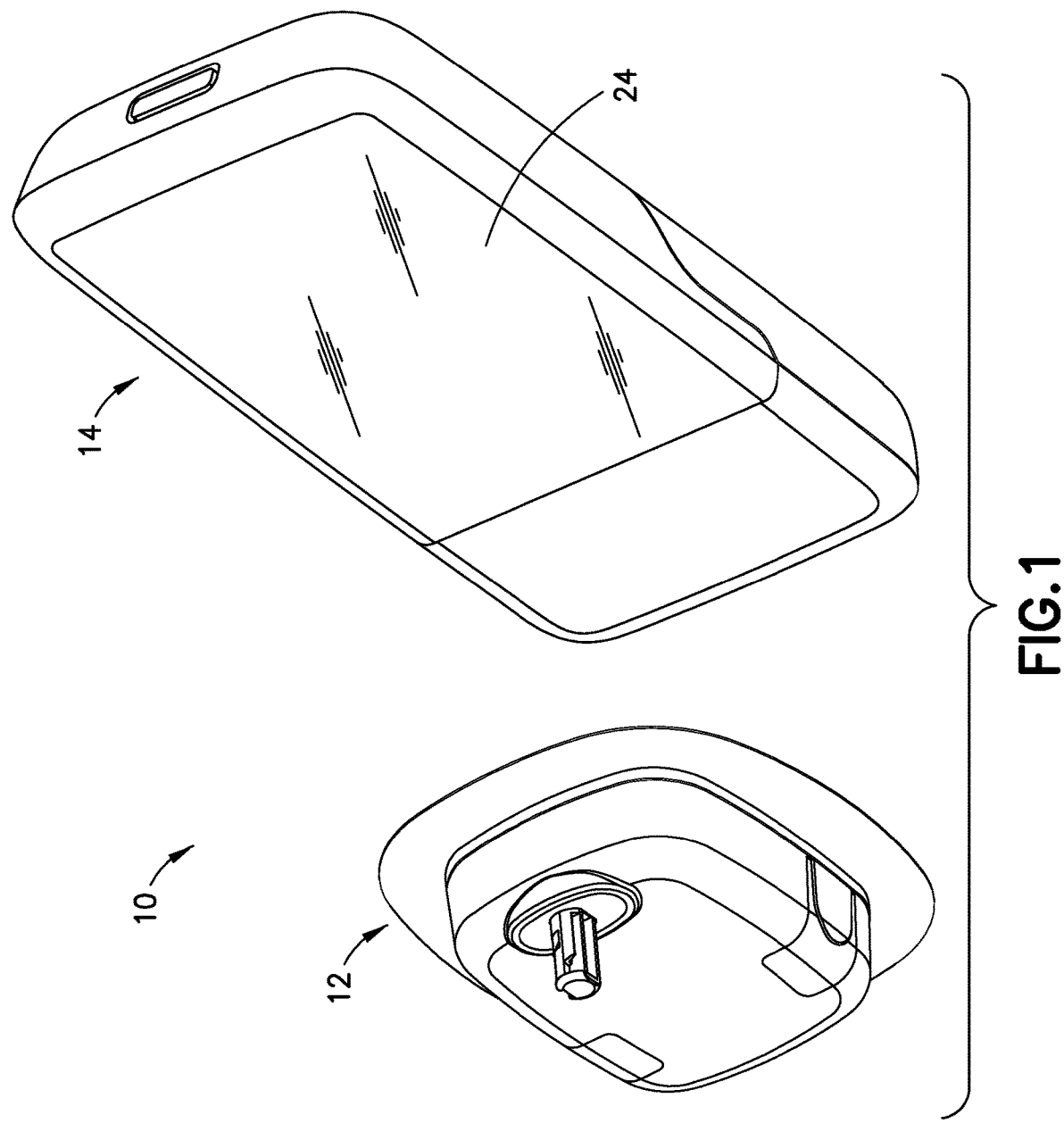

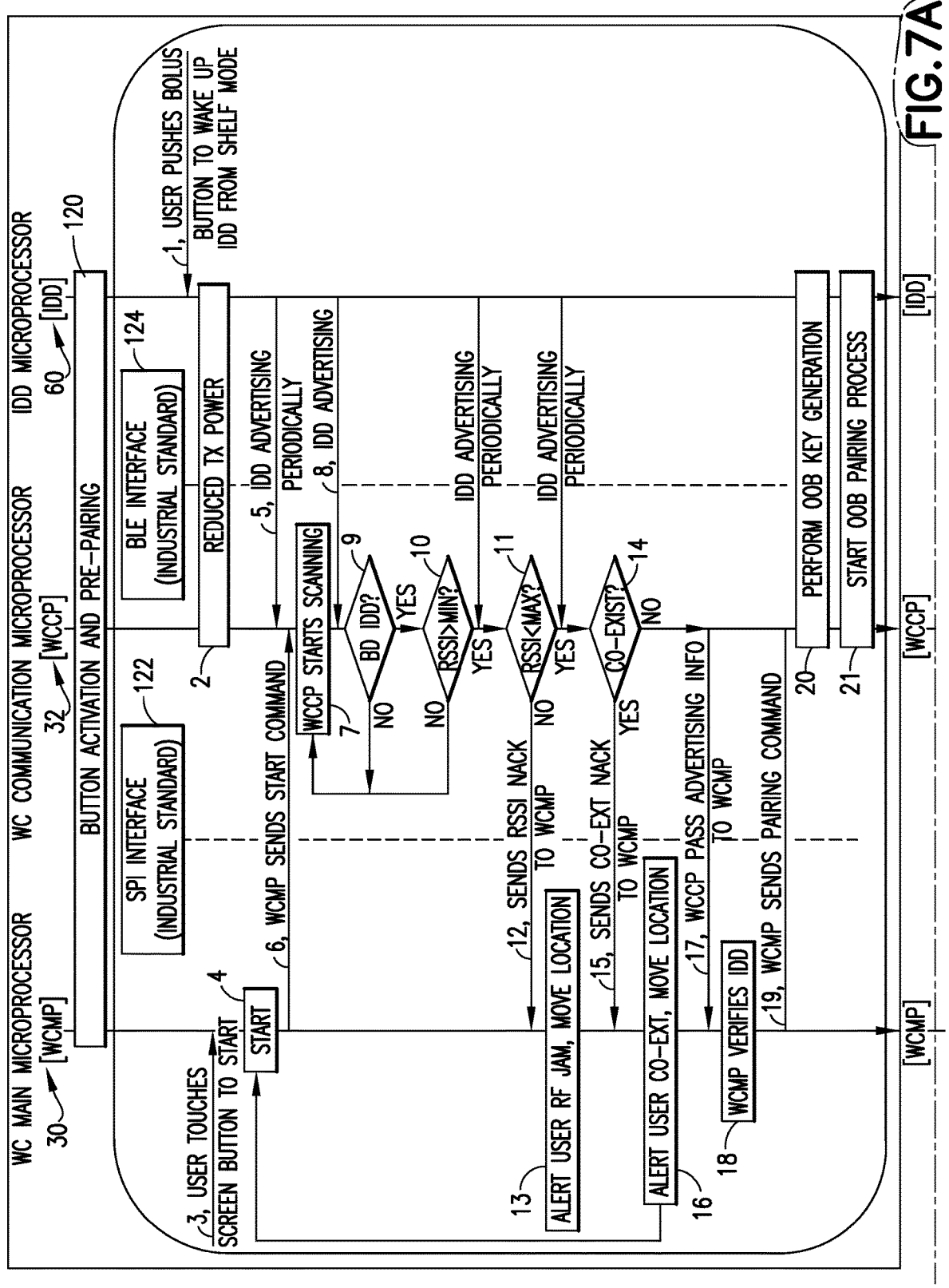

| FIG.7A |
| FIG.7B |

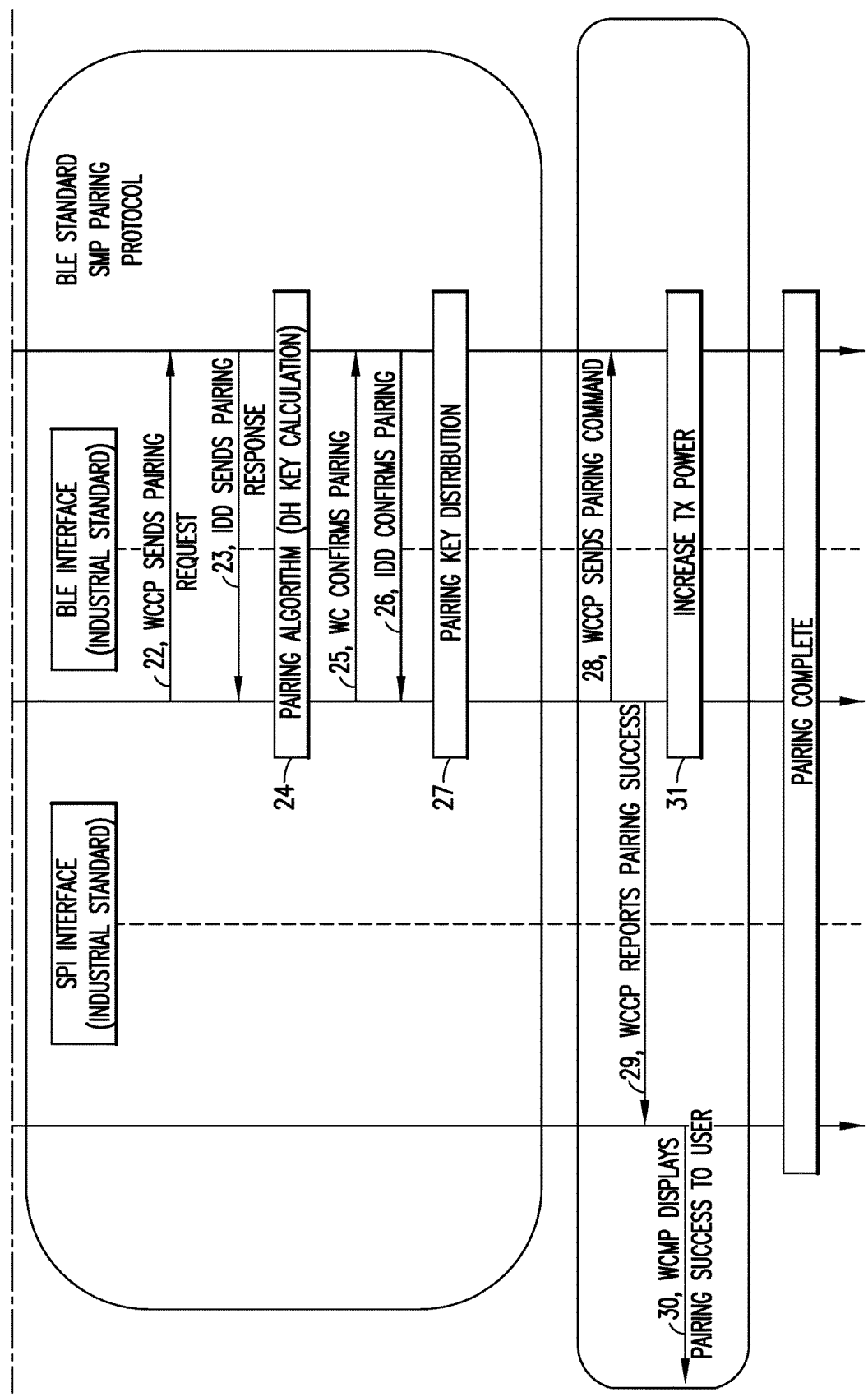

SYSTEMS, APPARATUSES AND METHODS FOR SECURE WIRELESS PAIRING BETWEEN TWO DEVICES USING EMBEDDED OUT-OF-BAND (OOB) KEY GENERATION

This application is a continuation of U.S. patent application Ser. No. 16/613,033, filed Nov. 12, 2019, which is based on PCT Application No. PCT/US2018/033614, filed May 21, 2018, which claims the benefit of U.S. Provisional Application Ser. No. 62/509,383, filed May 22, 2017, the entire contents of which are incorporated herein by reference.

TECHNICAL FIELD

The present disclosure relates to systems, methods and apparatuses for secure wireless pairing between two devices using embedded out-of-band (OOB) key generation to minimize pairing between a device and an unintended device and malicious interference with a paired device.

BACKGROUND

Demand for on-body medical devices (e.g., wearable infusion pumps) and body area network (BAN) medical devices (e.g., handheld blood glucose meters, smart phones with medical condition management apps, and wireless controllers for on-body devices) has been increasing along with an increase in patients' and healthcare providers' desire for better and more convenient patient management of medical conditions such as diabetes.

Secure pairing between two devices, such as between a wearable medical device and a separate dedicated controller or smart phone with (e.g., a smart phone with app related to operating the wearable medical device), is important to avoid unintended operations, or possibly malicious interference with the operations, of the medical device. Further, avoidance of pairing the medical device with another unintended device is also important, particularly when there are multiple potential devices with which a medical device can be paired within the same area.

Bluetooth Smart or Bluetooth Low Energy (BLE) technology provides an effective, low power protocol for wirelessly connecting devices, including devices that run on power sources such as coin cell batteries as can often be the case with wearable devices. Bluetooth Smart or BLE currently has three pairing options, that is, Passkey Entry, Just Works and OOB (Out-of-Band), which may or may not be used with various devices depending on different factors such as a device's input/output (IO) capabilities, and the level of required security needed for the application or function of the paired devices. For example, BLE devices that do not have IO capabilities of either physical IO or near field communication (NFC) capability cannot use the OOB pairing method because OOB authentication data needs to be input to the peer devices by the user. On the other hand, neither of the Just Work pairing and Passkey Entry pairing options have proven to be sufficiently secure for many wireless applications such as medical applications that require a high level of security and therefore more secure ways of pairing.

SUMMARY

The above and other problems are overcome, and additional advantages are realized, by illustrative embodiments of the present invention. Illustrative embodiments provide an OOB key generation method (e.g., for use with OOB pairing) whereby the devices to be paired do not require an IO functionality to enter authentication data. Illustrative embodiments also provide an embedded OOB key generation method to securely pair an on-body and/or drug delivering device with wireless or mobile devices whereby the on-body and/or drug delivering device does not require a display or key input device to enter authentication data, thereby simplifying its design and reducing its cost.

It is an aspect of illustrative embodiments of the present invention to provide a method of key generation for securely pairing a first device with a second device for wireless communication therebetween comprising providing each of the first device and the second device with a credential and a hash function; the first device transmitting advertising signals at selected intervals and in a selected radio frequency range via a first antenna; the second device scanning in the selected radio frequency via a second antenna; the first device providing data to be shared with the second device in the advertising signals; the second device receiving the shared data via the scanning; and the second device and the first device each using the shared data and the credential as input to the hash function to generate a key, the key generated by the first device being identical to the key generated by the second device.

In accordance with aspects of illustrative embodiments of the present invention, the providing comprises preconfiguring the first device and the second device with the credential and the hash function.

In accordance with aspects of illustrative embodiments of the present invention, the credential is a predefined 128-bit secret key.

In accordance with aspects of illustrative embodiments of the present invention, the advertising signals are generated and transmitted in accordance with Bluetooth Low Energy (BLE) specifications.

In accordance with aspects of illustrative embodiments of the present invention, the hash function is a secure hashing algorithm selected from the group consisting of AES-128 or SHA-256.

In accordance with aspects of illustrative embodiments of the present invention, the shared data is unique to first device and comprises at least one of a media access control (MAC) address, and a dynamic unique parameter.

In accordance with aspects of illustrative embodiments of the present invention, the key is a 128-bit out of band (OOB) key.

In accordance with aspects of illustrative embodiments of the present invention, the selected radio frequency range can be 2.40-2.48 Gigahertz (GHz) range.

It is an aspect of illustrative embodiments of the present invention to provide a device for securely pairing with a second device for wireless communication therebetween comprising: a memory device configured to store a credential and a hash function; a radio frequency (RF) interface for transmitting and receiving RF signals via at least one antenna; and a controller. The controller is configured to transmit advertising signals at selected intervals and in a selected radio frequency range via the RF interface and the antenna. The advertising signals comprise data to be shared with a second device. The controller inputs the shared data and the credential into the hash function to generate a key. The key generated by the device is identical to a key generated by the second device when it scans for and receives the advertising signals with the share data from the device.

It is an aspect of illustrative embodiments of the present invention to provide a device for securely pairing with a second device for wireless communication therebetween comprising: a memory device configured to store a credential and a hash function; a radio frequency (RF) interface for transmitting and receiving RF signals via at least one antenna; and a controller. The controller is configured to scan for and receive, via the RF interface and the antenna, advertising signals that are transmitted by a second device at selected intervals and in a selected radio frequency range. The advertising signals comprise data from the second device to be shared with the device. The controller inputs the shared data and the credential into the hash function to generate a key. The key generated by the device is identical to a key generated by the second device.

In accordance with aspects of illustrative embodiments of the present invention, the device and the second device are preconfigured with the credential and the hash function.

In accordance with aspects of illustrative embodiments of the present invention, the credential is a predefined 128-bit secret key.

In accordance with aspects of illustrative embodiments of the present invention, the advertising signals are generated and transmitted in accordance with Bluetooth Low Energy (BLE) specifications.

In accordance with aspects of illustrative embodiments of the present invention, the hash function is a secure hashing algorithm selected from the group consisting of AES-128 or SHA-256.

In accordance with aspects of illustrative embodiments of the present invention, the shared data is unique to whichever of the device and the second device that transmits the advertising signals. The shared data comprises at least one of a media access control (MAC) address, and a dynamic unique parameter associated with the corresponding one of the device and the second device that transmits the advertising signals.

In accordance with aspects of illustrative embodiments of the present invention, the key is a 128-bit out of band (OOB) key.

Additional and/or other aspects and advantages of illustrative embodiments of the present invention will be set forth in the description that follows, or will be apparent from the description, or may be learned by practice of illustrative embodiments of the present invention. Illustrative embodiments of the present invention may comprise devices to be paired and methods for operating same having one or more of the above aspects, and/or one or more of the features and combinations thereof. Illustrative embodiments of the present invention may comprise one or more of the features and/or combinations of the above aspects as recited, for example, in the attached claims.

BRIEF DESCRIPTION OF THE DRAWINGS

The above and/or other aspects and advantages of embodiments of the invention will be more readily appreciated from the following detailed description, taken in conjunction with the accompanying drawings, of which:

FIG. 1 depicts a medical device and a controller in accordance with an illustrative embodiment of the present invention;

FIGS. 7A and 7B are diagrams of operations of the medical device and the controller depicted in FIGS. 2A and 2B and in accordance with an illustrative embodiment of the present invention; and FIGS. 8A and 8B are diagrams of operations of the medical device and the controller depicted in FIGS. 2A and 2B and in accordance with another illustrative embodiment of the present invention.

Throughout the drawing figures, like reference numbers will be understood to refer to like elements, features and structures.

DETAILED DESCRIPTION OF ILLUSTRATIVE EMBODIMENTS

Figure 2A:
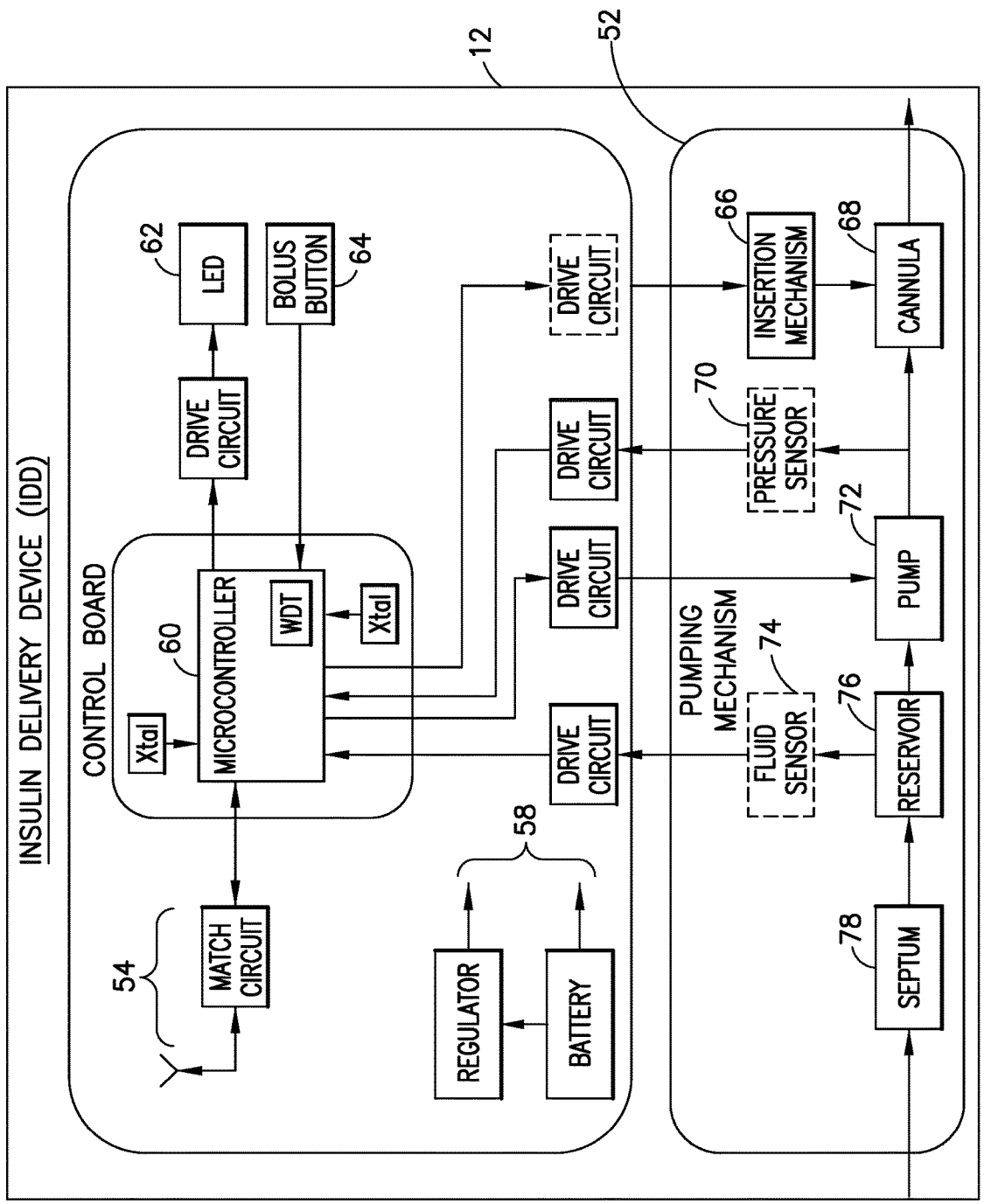
FIGS. 2A and 2B are block diagrams of the medical device and the controller in accordance with an illustrative embodiment of the present invention.

Reference will now be made in detail to embodiments of the present invention, which are illustrated in the accompanying drawings. The embodiments described herein exemplify, but do not limit, aspects of the present invention by referring to the drawings.

Figure 2B:
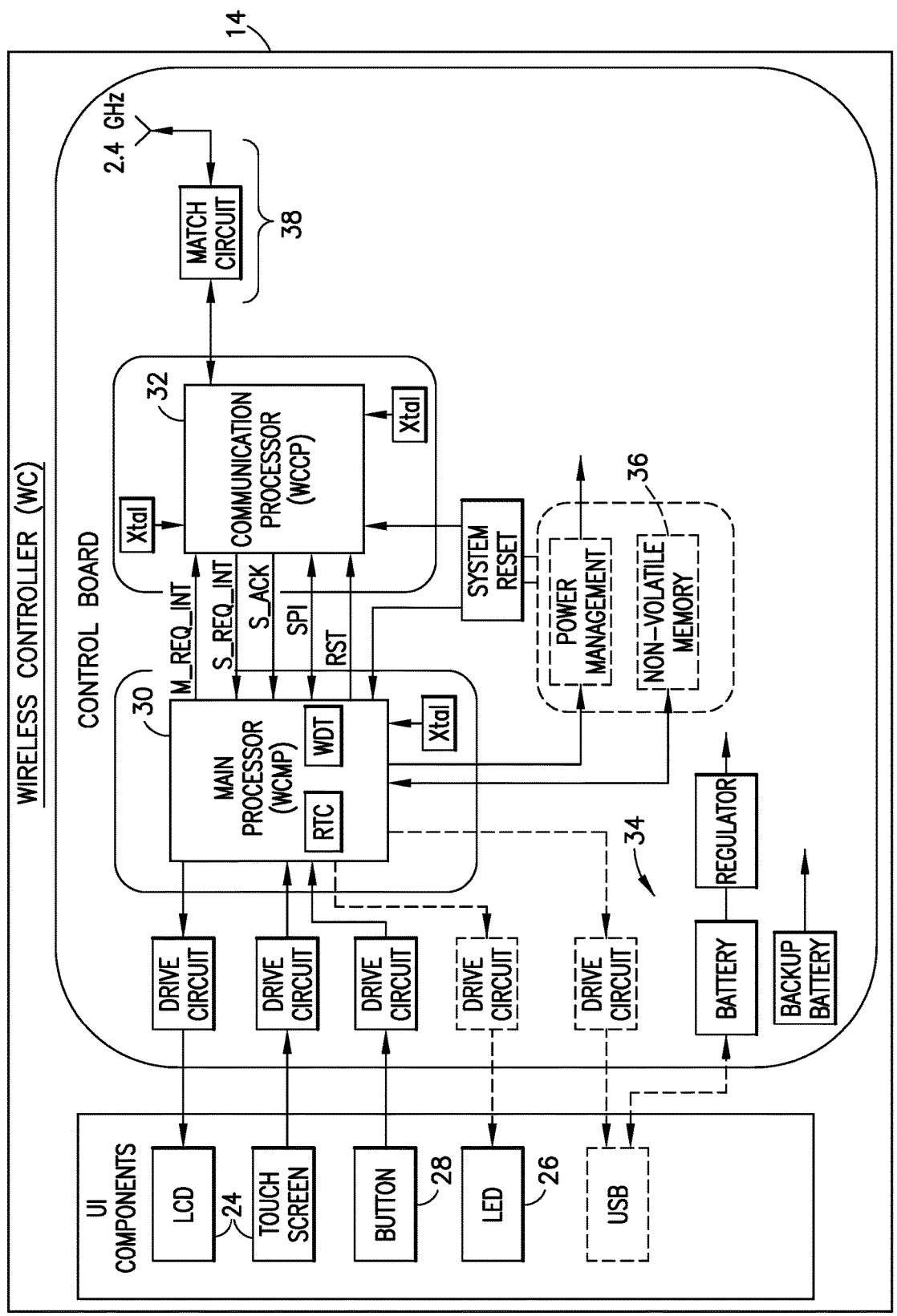

With reference to FIGS. 1, 2A and 2B, an illustrative medication delivery system 10 is shown having a medical device 12 and a controller 14 with display 24 or other user interface.

The medical device 12 can be a wearable device or a patient-carried device. The medical device 12 can have an integrated user interface as its controller 14, or the medical device can be configured to be controlled by a separate controller device such as a wireless controller 14 as shown in FIG. 1. In the illustrated embodiment, the medical device 12 is controlled by a wireless controller 14, but it is to be understood that aspects of illustrative embodiments of the present invention apply to a medical device 12 with its own controller and another device 14 to be paired with the medical device 12. Further, the wireless controller 14 can be a smart phone, for example.

For example, the medical device 12 can be a disposable insulin delivery device (IDD) for single patient use that is configured for continuous subcutaneous delivery of insulin at set and variable basal (24-hour period) rates and bolus (on-demand) doses for the management of patients with Type 2 Diabetes Mellitus (T2DM) requiring insulin therapy. It is to be understood, however, that the medical device 12 can be any on-body medical device (e.g., wearable infusion pump, continuous glucose meter) or body area network (BAN) medical devices (e.g., handheld blood glucose meter, smart phone with medical condition management apps, or wireless controller for on-body device).

As described below, an embedded OOB key generation process is described in accordance with an illustrative embodiment of the present invention and with reference to FIG. 9 that enhances the security of a BLE standard pairing protocol illustrated in FIG. 7B or FIG. 8B. It is to be understood that the range-based pre-pairing process described in connection with FIG. 7A or FIG. 8A need not be implemented via the devices 12 and 14 for pairing in order to realize the benefits of the OOB key generation process of FIG. 9. The OOB pairing option of the BLE standard pairing protocol is employed since it provides more security than the Just Work and Passkey Entry pairing options of BLE.

With continued reference to FIGS. 1, 2A and 2B, the IDD 12 is part of a system 10 that is an advanced insulin delivery system for use by patients with Type 2 Diabetes Mellitus (T2DM). It is configured for 24-hour-a-day use in all environments typically inhabited by the target users. It is configured for the patient user to wear the IDD for a period of three days (up to 84 hours). It has four (4) main functions: delivering user-set daily basal insulin rate; delivering user-set bolus insulin amount; delivering manual bolus insulin dose(s); and generating system status and notifications. The system addresses an unmet need for many Type 2 patients on multiple daily injections (MDI) requiring a discreet, simple and cost effective insulin delivery alternative to the traditional complex insulin pump. It is to be understood, however, that the medical device 12 can be used to deliver any type of fluid and is not limited to insulin delivery.

The Wireless Controller (WC) 14 is used to program the body-worn IDD to deliver a daily basal insulin rate and meal-time insulin amount to the patient. The WC 14 also provides status information of the IDD 12 as well as notifications to the user. The body-worn IDD 12 stores and administers insulin to the patient subcutaneously. The IDD sends feedback to the patient via the WC if it detects issues (e.g., low volume in the reservoir, low battery). An important function supported by communication software in the system 10 is the wireless communication between the WC 14 and IDD 12, which enables the IDD 12 to provide the feedback to the WC 14 and for the user to control their insulin delivery by the IDD 12 wirelessly via the WC 14 in a simple and discreet way.

In the illustrated embodiment shown in FIG. 2A, the IDD 12 has a microcontroller 60 configured to control a pumping mechanism 52, wireless communication with the WC (e.g., via an RF circuit 54 having a match circuit and antenna), and pump operations. The IDD has a bolus button(s) 64 for manual delivery of medication in addition to programmed delivery of medication. The pumping mechanism 52 comprises a reservoir 76 for storing a fluid medication (e.g., insulin) to be delivered via a cannula 68 to the patient wearing the IDD, and a pump 72 for controllably delivering designated amounts of medication from the reservoir through the cannula. The reservoir 76 can be filled via a septum 78 using a syringe. The IDD has a manual insertion mechanism 66 for inserting the cannula 68 into a patient; however, the processor 60 can be configured to operate an optional drive circuit to automate operation of the insertion mechanism 66 to deploy the cannula 68 into the patient. Further, the IDD 12 can be optionally provided with a fluid sensor 74 or a pressure sensor 70. An LED 62 can be operated by the microcontroller 60 to be on or flash during one or more pump operations such as during reservoir priming, for example. The IDD 12 is powered by a battery and regulator as indicated at 58. When initializing the IDD 12 (e.g., powering on to begin pairing with the WC 14), the bolus button(s) 64 can be configured as wake-up button(s) that, when activated by the user, causes the IDD 12 to wake from a power conserving shelf mode.

In the illustrated embodiment shown in FIG. 2B, the WC 14 is implemented as a dual microprocessor component having: 1) a WC Main Processor (WCMP) 30, and a WC Communications Processor (WCCP) 32. The WCMP 30 is connected to the user interface (UI) components such as the LCD display with touch screen 24, one or more buttons 28, LED indicator 26, and the like. The WCCP 32 is connected to radio frequency (RF) components 38 (e.g., an antenna and a match circuit) and is mainly responsible for the WC 14's wireless communication with the IDD 12. The two processors 30, 32 communicate with each other through a serial peripheral interface (SPI). The two processors 30, 32 can also interrupt each other through two interrupt pins, M_REQ_INT and S_REQ_INT.

With continued reference to FIG. 2B, the WC 14 is designed to be non-field serviceable (i.e. no parts to be inspected, adjusted, replaced or maintained by the user), except for replaceable alkaline batteries 34 for power. A non-volatile memory (e.g., FLASH memory) 36 is provided in the WC to store delivery and status data received from the IDD 12 such as delivery dates and times and amounts.

The LCD with capacitive touch screen 24 serves as the visual interface for the user by rendering visual and graphical outputs to the user (e.g., system information, instructions, visual notices, user configurations, data outputs, etc.), and by providing a visual interface for the user to enter inputs (e.g., device operation inputs such as IDD pairing and set up and dosing, and configuration parameters, and so on). The WC display with capacitive touch screen 24 detects (at least) single-touch gestures over its display area. For example, the touch screen is configured for recognizing user tactile inputs (tap, swipe, and button press), allowing for navigation within UI screens and applications. The touch screen 24 aids in executing specific system functionalities (i.e. IDD 12 setup and pairing with the WC 14, insulin dosing, providing user with dosing history, and IDD deactivation and replacement with another IDD, and so on) through specific user interactions. The WC 14 can also include a button 28 such as a device wake-up button that, when activated by the user, causes the WC 14 to wake from a power conserving sleep mode. The WC 14 can also have an LED 26 to indicate low battery status (e.g., indicate low battery state when there is 12 hours or less of usage remaining).

Figure 3:
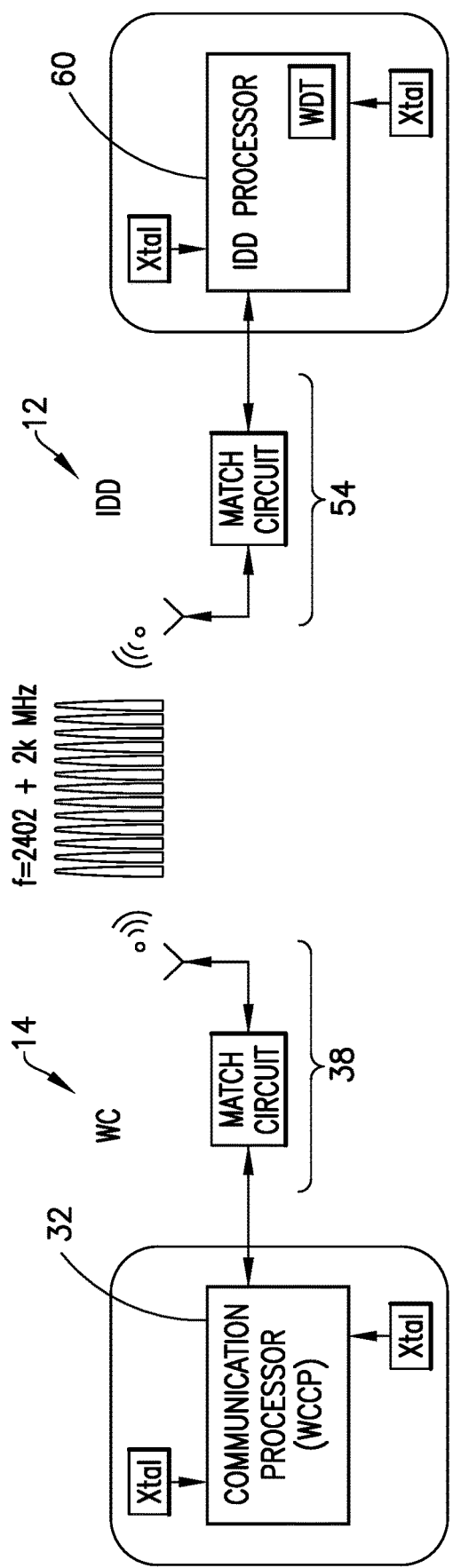
FIG. 3 is depicts radio frequency (RF) components of the medical device and the controller depicted in FIGS. 2A and 2B and in accordance with an illustrative embodiment of the present invention.

The WC 14 radio frequency (RF) interface with the IDD 12 is, for example, based on a Bluetooth® Low Energy or BLE-based communication protocol, although other wireless communication protocols can be used. In the medication delivery system 10, the WC 14 and IDD 12 communicate wirelessly within a distance of up to 10 feet or approximately 3 meters, utilizing the ISM band from 2400 MHz to 2480 MHZ spectrum. The WC 14 communicates with the IDD 12 while the IDD is adhered to the body in open air. The WC 14 is the central device or master, and the IDD 12 is the peripheral device or slave. Whenever the WCMP 30 wants to send information to the IDD 12 or retrieve information from the IDD 12, it does so by interacting with the WCCP 32, which in turn, communicates with the IDD 12 across the BLE link via the respective RF circuits 38 and 54, as shown in FIG. 3.

In accordance with an illustrative embodiment of the present invention, the WC 14 (e.g., its WCCP 32) and the IDD 12 communicate in accordance with a protocol and various operations to mitigate risk that the WC 14 pairs with an unintended IDD 12' or, vice versa, that an intended IDD 12 pairs with an unintended WC 14'. Either case could cause unintended operation of the pump mechanism 53, potentially resulting in insulin over-infusion which can be injurious to the patient. In accordance with illustrative aspects of the system 10, the communication range at IDD 12 startup (e.g., before pairing) is reduced, unintended devices such as an unintended IDD 12' are rejected by the WC 14 and, when multiple IDD co-existences are detected nearby, the WC 14 is prevented from pairing with an IDD 12 unless that IDD 12 is the only IDD detected by the WC 14. As described in more detail below, example operations in the system 10 comprise reducing the transmit power level of the WC 14 and the IDD 12 to control the communication range (e.g., to less or equal to 20″ before pairing), using signal strength indicators (e.g., the minimum and maximum Received Signal Strength Indicator (RSSI) thresholds) to reject the unintended devices including the unintended IDDs 12', adjusting WC 14 startup scanning time to detect multiple IDD co-existence, instructing the user to move to other room or location with his/her WC 14 and IDD 12 to retry the pairing when more than one IDDs 12 are detected, and only allowing the WC 14 to pair with the IDD 12 when it is the only IDD 12 detected by the WC 14.

Figure 4:
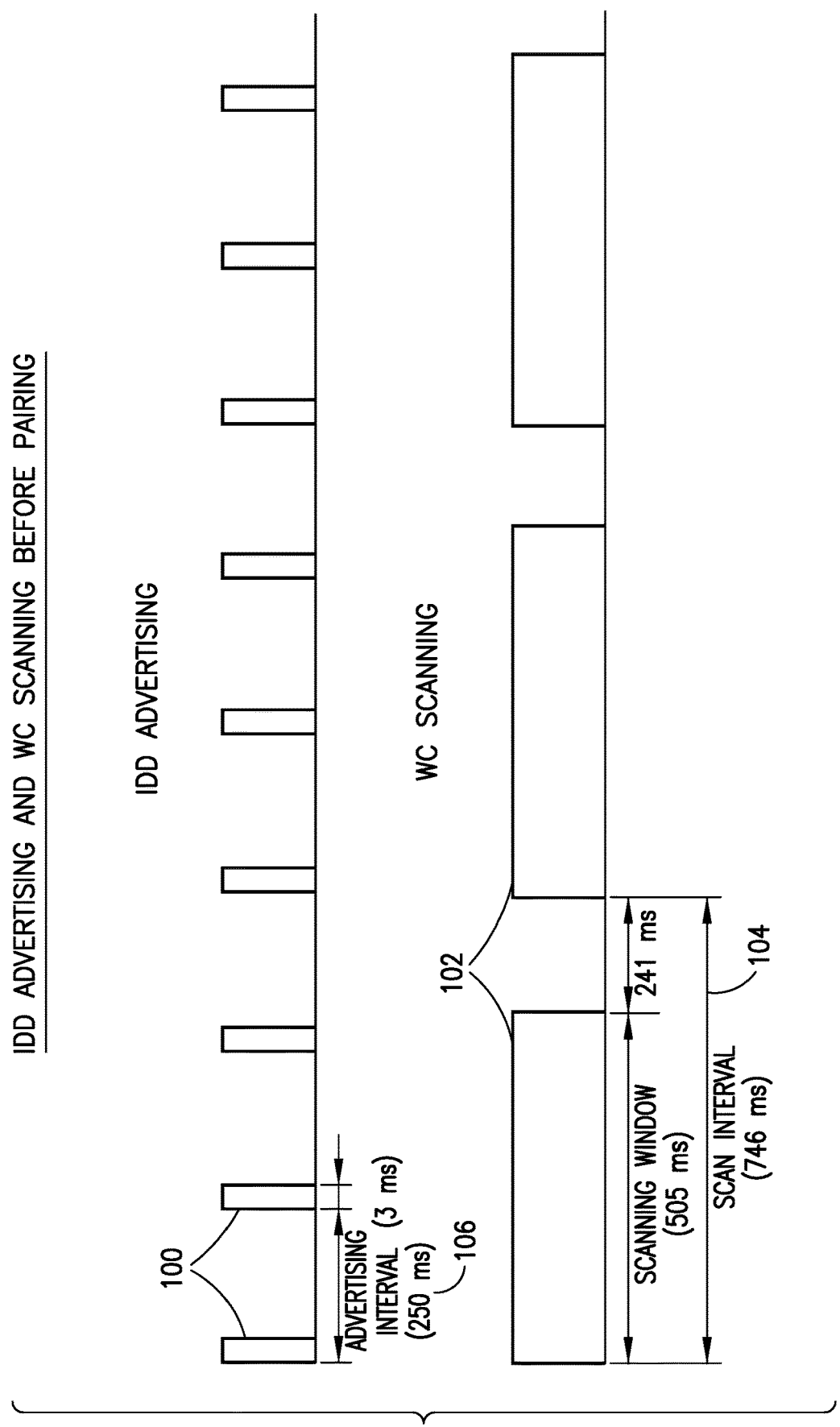
FIGS. 4, 5 and 6 are diagrams of signals transmitted from the medical device and the controller in accordance with an embodiment of the present invention.

IDD 12 advertising and WC 14 scanning before pairing are illustrated in FIG. 4 and in accordance with an illustrative embodiment of the present invention. Upon waking up and before pairing, every 250 ms (+/−10%) as indicated at 106, the IDD 12 advertises with IDD Startup Advertising Data packets 100, and waits for 3 ms (+/−10%) for the possible reply from a WC 14. At the WCMP 30's request, the WCCP 32 initiates the communication by starting scanning the IDD advertisement every 746 ms (+/−10%) 104 for about a 505 ms (+/−10%) scanning window 102. At the end of the scanning period 104, WCCP 32 performs a co-existence check as described below in connection with FIGS. 7 and 8. At the end of the scanning time period 104, if the WCCP 32 does not detect any advertising packet 100 within a transport layer timeout period, the WCCP stops scanning and sends a Nack response with a Transmission Timeout error code. As described below in connection with FIGS. 7 and 8, after sending a Nack response, the WCCP 32 goes to sleep if not advertising is detected.

Figure 5:
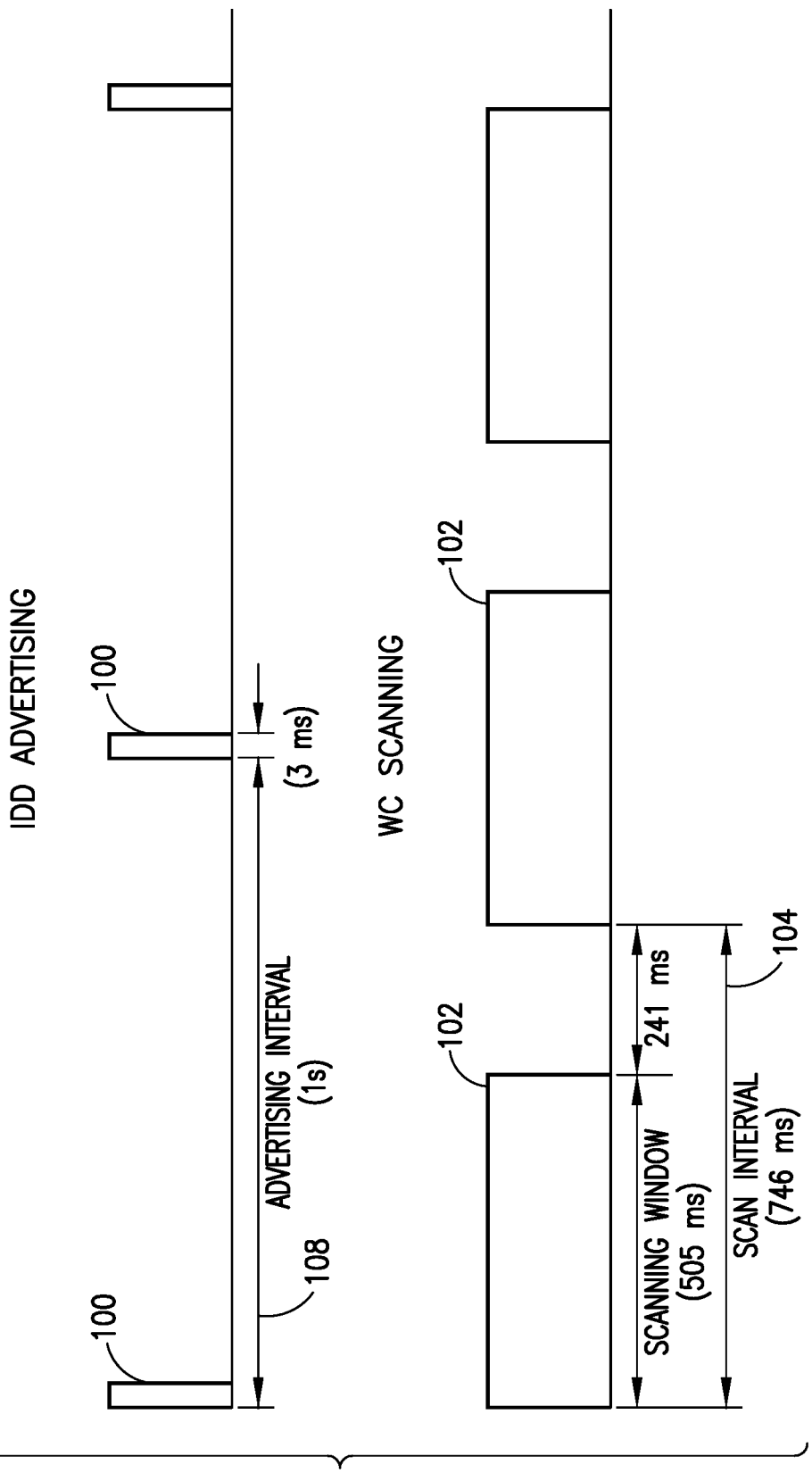

IDD 12 advertising and WC 14 scanning after pairing are illustrated in FIG. 5 and in accordance with an illustrative embodiment of the present invention. After pairing, if the IDD 12 is not actively pumping, it advertises with a IDD Periodic Data Packet 100 at a selected interval 108 (e.g., every 1 second (+/−10%)). After each advertisement 100, the IDD 12 waits for 30 ms (+/−10%) for the possible reply from the WC 14. After pairing, at the WCMP 30's request, the WCCP 32 initiates the communication by starting scanning the IDD advertisement every 746 ms (+/−10%) 104 for a 505 ms (+/−10%) scanning window 102.

Figure 6:
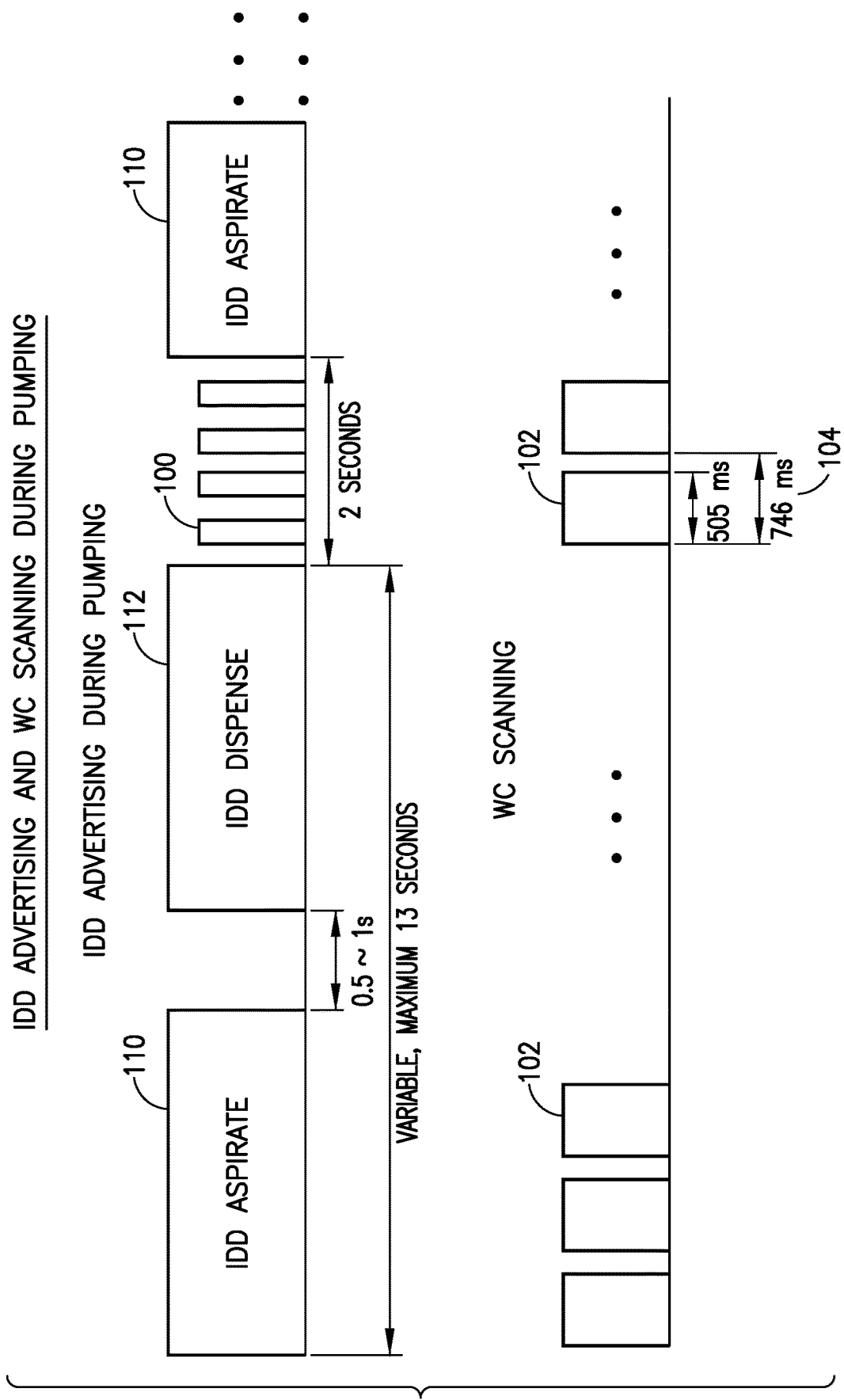

IDD 12 advertising and WC 14 scanning during pumping are illustrated in FIG. 6 and in accordance with an illustrative embodiment of the present invention. If the IDD 12 is delivering a medication such as insulin, it advertises every 500 ms for 2 seconds at the end of a dispense stroke 112. Even though it is not indicated in FIG. 6, during the break time between IDD aspirate periods 110 and dispense periods 112, the IDD 12 still tries advertising if possible. When the IDD 12 is pumping, at the WCMP 30's request, the WCCP 32 initiates the communication by starting scanning the IDD advertisement every 746 ms (+/−10%) 104 for 505 ms (+/−10%) scanning windows 102.

Figures 7, 7B:
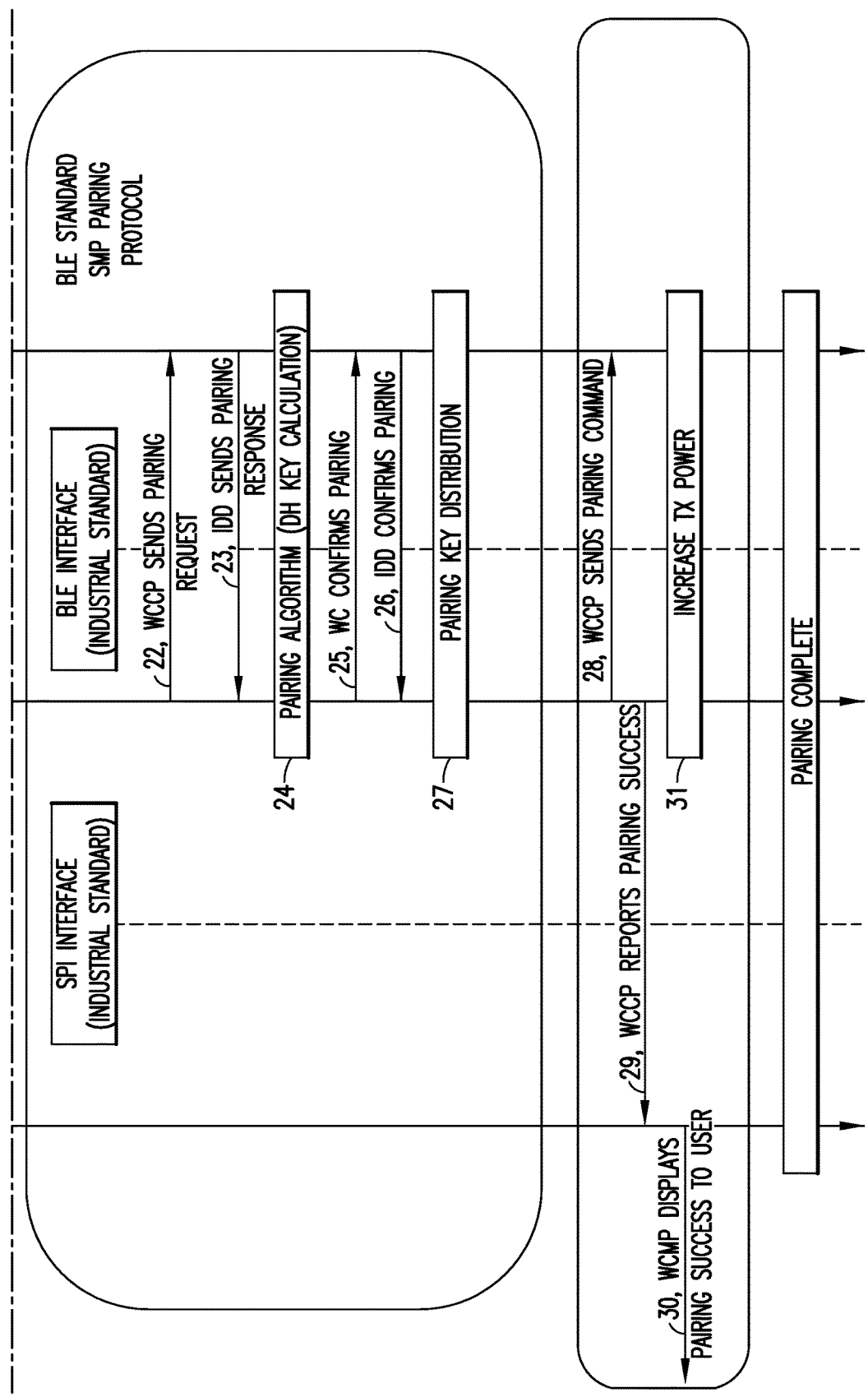

With reference to FIGS. 7A and 7B, operations are described for the WC 14 and IDD 12 and in particular with respect to the WCMP 30, WCCP 32 and IDD processor 60. An SPI interface between the WCMP 30 and WCCP 32 is shown; however, as explained above, the WC 14 can be configured as a single processor device. Also, as described above, a BLE interface or similar wireless interface 124 is provided between the WC 14 and the IDD 60. The operations are numbered 1 through 30 in FIGS. 7A and 7B for ease of reference.

To commence pairing the WC 14 with an IDD 12, the IDD 12 can be awakened from a power conserving shelf mode (e.g., by a user activating button(s) 64), as indicated by operation 1 in FIG. 7A. The IDD 12 reduces its transmission power (operation 2), and starts advertising IDD Startup Advertising Data (operation 5) with the transmit power level 0 up to 1 minute+/−10%. The IDD 12 periodically transmits an IDD Startup Advertising Data packet (operation 8). The WC 14 can be awakened from its power conserving sleep mode (e.g., as indicated in operation 3) in response to a user activating a button such as a touch screen 24 start button or other button 28, and enter a start mode (operation 4) such as the WCMP 30 sending a Start command to the WCCP 32. Upon receiving the Start command, the WCCP 32 starts scanning for the IDD Startup Advertising Data (operation 6) as described above in connection with FIG. 4.

With continued reference to FIG. 7A and to operation 9, the WC 14 can determine if a particular type of device 12 is in its vicinity. For example, the IDD 12 Startup Advertising Data can comprise IDD identifying information (e.g., selected dynamic and/or static parameters or values that identify a type of device such as manufacturer and/or model or other characteristic) such that the WC 14 can be configured to only pair with devices or IDDs having designated IDD identifying information and not with other devices that do have the designated IDD identifying information. With reference to operation 9, the WCCP 32 can determine if the IDD 12 Startup Advertising Data has IDD identifying information relating, for example, to its particular manufacturer. If not, the WCCP 32 continues scanning (operation 7).

With reference to operation 10 in FIG. 7A, if the WCCP 32 scans IDD Startup Advertising Data from a device in its vicinity that does have the designated IDD identifying information, then the WCCP 32 commences determining if signal strength information pertaining to the IDD Startup Advertising Data meets one or more thresholds. For example, the WCCP 32 can stop scanning and perform a Receiving Signal Strength Indicator (RSSI) check on the received packet. The RSSI information can be generated, for example, by an RF chip in the RF circuit 38 of the WC 14. If the RSSI is less than a minimum level (e.g., −65 dBm+/−10%), the WCCP 32 ignores the received advertising packet, and retries the scanning process (operation 7). The minimum level is selected to differentiate an IDD 12 advertising in the vicinity of the WP 14 from noise or an IDD 12 that is far enough away from the WC 14 to be an unintended device for pairing.

With reference to operation 11 in FIG. 7A, if the RSSI is more than a maximum level (e.g., −3 dBm+/−10%) such as when an RF jam may have occurred, the WCCP 32 sends a Nack response to the WCMP 30 (e.g., a response with a Maximum RSSI Exceeded error code) as indicated at operation 12. The WCMP 30 can, in turn, generate an alert (e.g., via the LCD touch screen 24) to advise the user to move to another location (operation 13).

If, at the end of the scanning time period, the WCCP 32 detects the advertising packets from more than one IDD 12 (operation 14), the WCCP 32 sends a Nack response to the WCMP 30 (e.g., a response with a Co-existence Detected error code) (operation 15). The WCMP 30 can, in turn, generate an alert (e.g., via the LCD touch screen 24) to advise the user to move to another location to retry pairing, and optionally that another IDD has been detected (operation 16).

If the RSSI and co-existence checks have passed, the WCCP 32 can send an IDD Startup Advertising Data response message to the WCMP 30 (operation 17). Upon receiving the response message, the WCMP 30 verifies the IDD Startup Advertising Data (e.g., using the designated IDD identifying information) (operation 18). If this IDD compatibility check is successful, the WCMP 30 sends a Pairing command message to the WCCP 32 (operation 19). Upon receiving the Pairing command, the WCCP 32 can perform a IPC sanity check on the pairing command message before performing out-of-band (OOB) key generation (operation 20) in accordance with illustrative embodiments of the present invention.

With reference to operation 21 in FIG. 7A, a pairing process (e.g., the Bluetooth Low Energy OOB pairing method) is initiated between the IDD 12 and the WC 14. For example, as indicated at operations 22 and 23 in FIG. 7B, the IDD 12 can receive a Pairing request, and perform a sanity check that causes the IDD 12 to ignore the request if the sanity check fails, and to send a pairing response to the WCCP 32 if the sanity check succeeds. The IDD 12 and WCCP 32 can each perform a Pairing algorithm (operation 24) (e.g., Bluetooth Low Energy (BLE) pairing). The pairing keys can be generated on the IDD 12 and WCCP 32 separately such that the air interface is not needed for pairing key exchange. The WCCP 32 saves the pairing key information to a nonvolatile memory location. The WCCP 32 confirms pairing by sending a low level confirmation packet to the IDD (operation 25). Upon receiving the WCCP 32's confirmation packet, the IDD 12 saves the pairing key information. Upon receiving the WCCP's confirmation packet, the IDD confirms the pairing by sending a low level confirmation packet back to the WCCP 32 (operation 26). Thus, the WCCP 14 and the IDD 32 facilitate the pairing key distribution (operation 27).

With continued reference to FIG. 7B, upon completion of pairing (e.g., according to BLE standard Security Manager Protocol (SMP) pairing), the WCCP 32 sends a pairing command to the IDD 12 (e.g., to perform transport layer pairing once low level pairing is completed) (operation 28). Upon receiving the IDD's confirmation packet, the WCCP 32 sends the Pairing Success message to the WCMP 30 (operation 29). Upon receiving the Pairing Success message, the WCMP 30 saves the pairing key information to a nonvolatile memory location for the record and can display pairing success on a user interface (operation 30). After pairing, IDD transmit power level is set (e.g., to 15) to increase the communication range (operation 31). Further, after pairing, the WCCP 32 transmit power level is also increased. The WC 14 only communicates with the paired IDD 12, and the IDD 12 only accepts a command from the paired WC 14. This bonded communication relationship of the WC 14 and IDD 12 remains until the IDD is deactivated. After IDD deactivation, the WC 14 is free to pair with a new IDD 12; however, at any given time, the WC 14 is preferably only allowed to pair with one IDD 12.

Figure 8A:
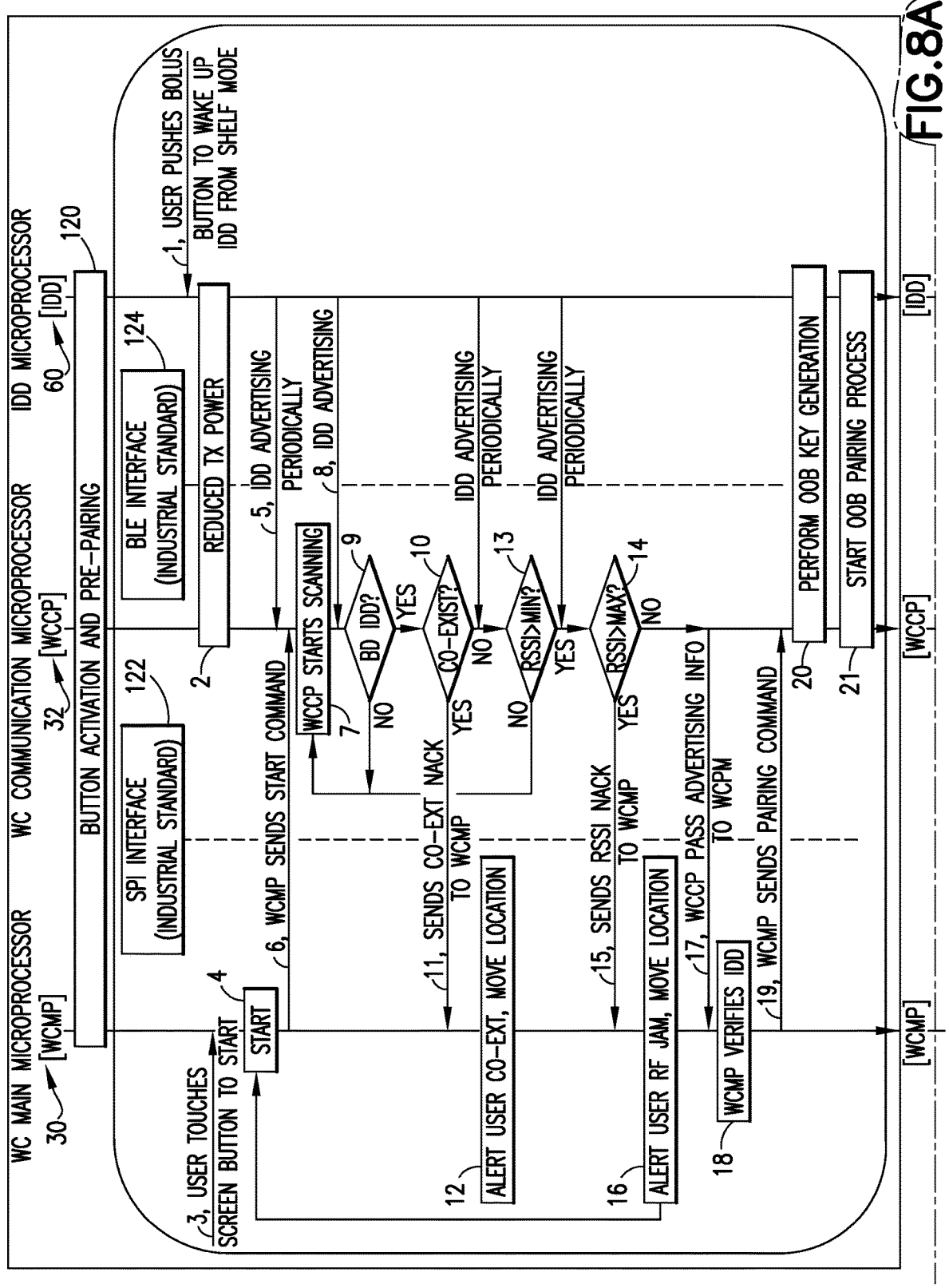

The WC 14 and IDD 12 operations in FIGS. 8A and 8B are similar to those in FIGS. 7A and 7B, except that the co-existence check (operation 10) occurs before the signal strength (e.g., RSSI) checks (operations 13 and 14). In other words, the order of the co-existence and signal strength checks can be interchangeable. Also, the Device check (operation 9) can be optional.

In accordance with an aspect of the present invention, the WCCP 32 does not need to constantly scan (e.g., operation 7 of FIGS. 7A and 8A) which conserves WC 14 power. In other words, scanning by the WCCP can be interleaved such that scanning occurs for a selected duration (e.g., a 505 ms scanning window 102 as shown in FIG. 4) that is longer than two advertising intervals 106 (e.g., two 250 ms advertising intervals 106) by the IDD 12 to ensure that the WCCP 32 will not miss detecting a IDD Startup Advertising Data packet 100 from an IDD 12 within pairing range of the WC 14. The WCCP then stops scanning for a selected interval of time (e.g, 241 ms in FIG. 4) within a scanning interval 104 before scanning again for another scanning window 102 of time within the next scanning interval 104.

If an IDD Startup Advertising Data packet 100 is detected during a scanning window 102, then the WCCP 32 stops scanning and commences one or more of the various checks described above in connection with FIG. 7A; that is, a device check (operation 9), received signal strength checks (operations 10 and 11) and a co-existence check (operation 14). If multiple devices are located via operation 14, or the other checks are not passed (i.e., operations 9, 10 and 11), then the WCCP 32 commences scanning again (operation 7).

If an IDD Startup Advertising Data packet 100 is not detected during a scanning window 102, then the WCCP 32 can scan over a series of scan intervals 104 for a selected amount of time (e.g., 10 seconds) and then timeout. Upon timeout, the WCCP 32 can send a Nack signal to the WCMP 30 which, in turn, alerts the user regarding a communication error and the need to being an intended IDD 12 closer to the WC 14 and retry pairing.

In accordance with an aspect of the present invention and with reference to FIG. 9, an enhancement (e.g., operation 20 in FIG. 7A and FIG. 8A) to the BLE standard pairing illustrated in FIGS. 7B and 8B will now be described to increase security using OOB key generation. First, a secure hashing algorithm (H) such as, for example, AES-128 or SHA-256 or other secure hash algorithm is used at each of the peer devices to be paired. Second, the inputs of the hashing function for the peer devices are configured to be the same so that an identical OOB key can be generated as the output of the hashing function at each of the peer devices. In order to build the same inputs to the hashing function at each peer device, a peer device (e.g., IDD 12) transmits some of its unique data to another peer device (e.g., the wireless controller 14) to share (i.e., hereinafter referred to as shared data) such as, for example, a MAC address and/or other dynamic unique parameters through advertisements 100. In addition, all of the devices that can be potentially paired (e.g., the IDDs 12, WCs or smart phone apps 14) share a credential, e.g., a 128-bit secret key. Using this shared data and the predefined secret key in the secure hash function as input, both peer devices 12,14 generate an identical 128-bit of OOB key, i.e., the authentication data for pairing. Dynamic parameters such as MAC address can be built as a variant (e.g., unique among the IDDs 12), and the 128-bit of secret key is shared and kept the same (e.g., the same as between the IDDs 12 and WC or smart phone apps 14). Therefore, the OOB key for each pair 12,14 of various sets of pairing devices is different and secure.

Figure 9:
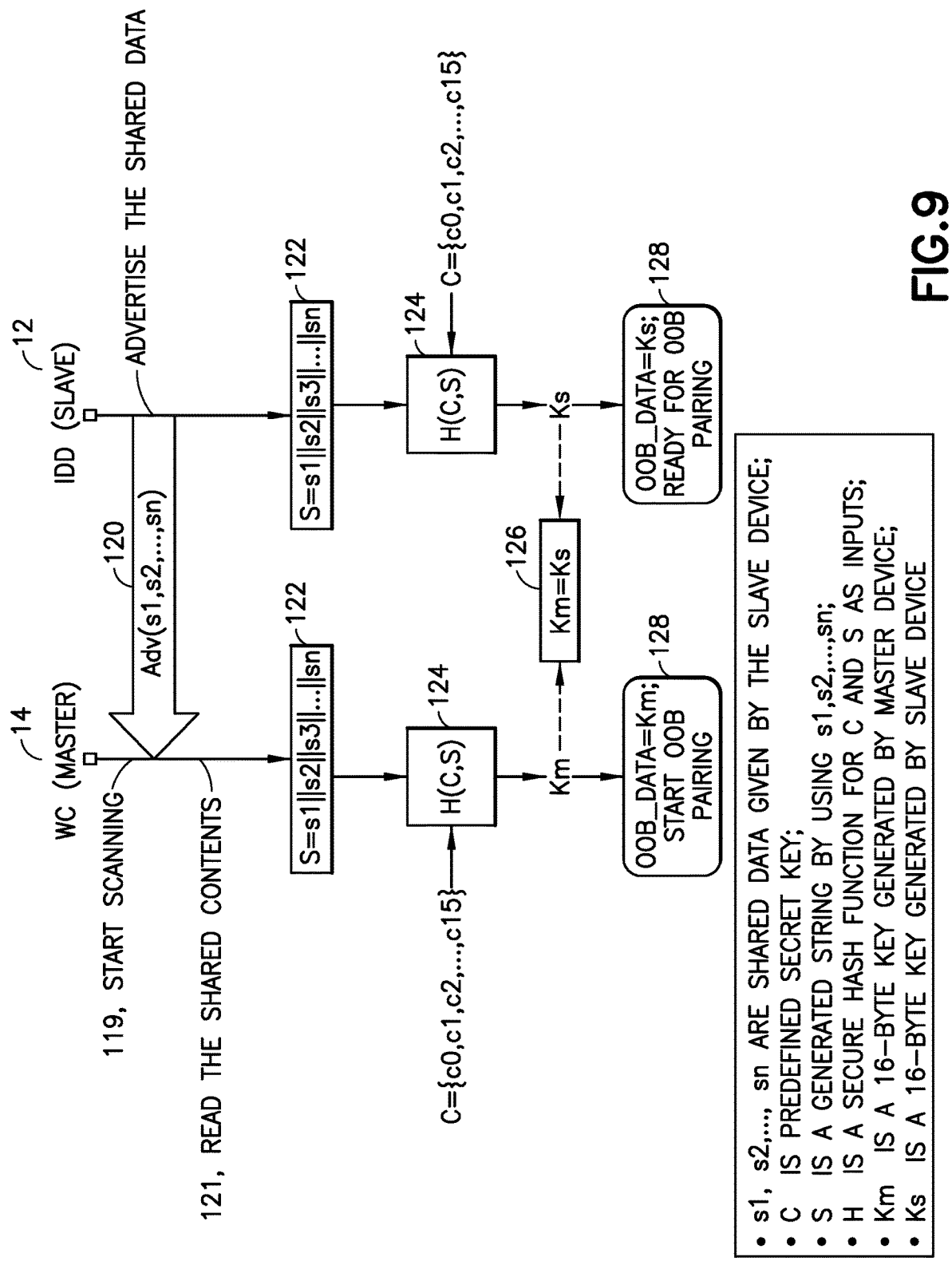
FIG. 9 is a diagram of operations of peer devices employing embedded Out-of-Band (OOB) key generation for secure wireless pairing in accordance with an illustrative embodiment of the present invention.

As shown in FIG. 9, a slave device (e.g., the IDD 12) and a master device (e.g., the wireless controller 14) are both provided with a predefined secret key (C), and a secure hash function (H). For example, both master and slave devices are programmed an identical 16-byte secret key C={c0, c2, ... c15}. The secret key C and the hash function H can be provided, for example, to IDDs and WC 14 at the time of manufacture, or to a smart phone 14 operating with the IDD at the time a corresponding app is installed that contains this information needed for key generation. The slave device prepares its unique shared data {s1, s2, s3, ..., sn}. As indicated at 120, each IDD 12 is configured to transmit advertising packets 100 to a WC 14 with which it wishes to pair. The advertising packets 100 contain that IDD's unique shared data $s_1, s_2, \ldots, s_n$. As indicated at 119, the master device starts scanning, and the slave device advertises the shared data $\{s1, s2, s3, \ldots, sn\}$. The master device reads the shared data from slave's advertisements, as indicated at 121, such that both the IDD and the WC compute the same input $S=s1\|s2\|s3\| \ldots \|sn$, as indicated at 122. The same inputs (i.e., shared data S and predefined key C) are provided to the same selected secure hash algorithm H provided at each of the peer devices, as indicated at 124, such that the IDD 12 and WC 14 each generate identical keys, as indicated at 126 (i.e., Km=H(C, S) and Ks=H(C, S); therefore, Km=Ks). Thus, OOB-data comprising a key is provided at each of the peer devices to commence OOB pairing with Km and Ks respectively, as indicated at 128.

The OOB key generation described in connection with FIG. 9 and in accordance with an illustrative embodiment of the present invention realizes a number of advantages. First, man-in-the-middle attacks and eavesdropping are prevented by using an OOB key generation method. Second, no IO capability is needed, allowing for simplified and less costly IDDs 12 or other medical devices that will not require, for example, a keypad and/or display for enter authentication data. Thus, the most secure pairing option of BLE (i.e., OOB pairing) is achieved without an IO capability in either of the peer devices. The OOB key generation described herein in accordance with illustrative embodiments of the present invention also prevents brute-force calculations since the OOB key generation algorithm is based on both dynamic and static inputs and therefore increases the difficulty of brute-force calculations.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

The components of the illustrative devices, systems and methods employed in accordance with the illustrated embodiments of the present invention can be implemented, at least in part, in digital electronic circuitry, analog electronic circuitry, or in computer hardware, firmware, software, or in combinations of them. These components can be implemented, for example, as a computer program product such as a computer program, program code or computer instructions tangibly embodied in an information carrier, or in a machine-readable storage device, for execution by, or to control the operation of, data processing apparatus such as a programmable processor, a computer, or multiple computers.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network. Also, functional programs, codes, and code segments for accomplishing illustrative embodiments of the present invention can be easily construed as within the scope of the invention by programmers skilled in the art to which the present invention pertains. Method steps associated with the illustrative embodiments of the present invention can be performed by one or more programmable processors executing a computer program, code or instructions to perform functions (e.g., by operating on input data and/or generating an output). Method steps can also be performed by, and apparatus of illustrative embodiments of the present invention can be implemented as, special purpose logic circuitry, e.g., an FPGA (field programmable gate array) or an ASIC (application-specific integrated circuit), for example.

The various illustrative logical blocks, modules, and circuits described in connection with the embodiments disclosed herein may be implemented or performed with a general purpose processor, a digital signal processor (DSP), an ASIC, a FPGA or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example, semiconductor memory devices, e.g., electrically programmable read-only memory or ROM (EPROM), electrically erasable programmable ROM (EEPROM), flash memory devices, and data storage disks (e.g., magnetic disks, internal hard disks, or removable disks, magneto-optical disks, and CD-ROM and DVD-ROM disks). The processor and the memory can be supplemented by, or incorporated in special purpose logic circuitry.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The above-presented description and figures are intended by way of example only and are not intended to limit the present invention in any way except as set forth in the following claims. It is particularly noted that persons skilled in the art can readily combine the various technical aspects of the various elements of the various illustrative embodiments that have been described above in numerous other ways, all of which are considered to be within the scope of the invention.

The invention claimed is:

1. A method of securely pairing a first device with a second device for wireless communication therebetween comprising:
   providing each of the first device and the second device with predefined data;
   the first device transmitting advertising signals at selected intervals and in a selected radio frequency range via a first antenna;
   the second device scanning in the selected radio frequency via a second antenna;
   the first device providing data to be shared with the second device in the advertising signals;
   the second device receiving the shared data via the scanning;
   the second device and the first device each using at least part of the shared data and at least part of the predefined data to generate an out of band [OOB] key, the OOB key generated by the first device being identical to the OOB key generated by the second device; and
   the second device and the first device performing OOB pairing with each other using their respective OOB key prior to performing short-range wireless communication paring.

2. The method of claim 1, wherein the predefined data is chosen from a credential and a hash function.

3. The method of claim 1, wherein the shared data comprises data unique to the first device.

4. The method of claim 1, wherein the shared data comprises first device identifying information.

5. The method of claim 1, further comprising the first device transmitting the advertising signals, and the second device scanning for the advertising signals, before pairing, the advertising signals comprising data packets.

6. The method of claim 5, wherein the data packets are configured in accordance with a short-range wireless communication protocol.

7. The method of claim 5, further comprising the second device performing designated functions using data chosen from the predefined data, and data provided in the data packets.

8. The method of claim 5, wherein data provided in the data packets comprises device identifying information.

9. The method of claim 1, further comprising the first device and the second device exchanging data packets with each other after OOB pairing.

10. The method of claim 9, wherein the data packets are configured in accordance with a short-range wireless communication protocol.

11. The method of claim 9, wherein the data packets transmitted from at least one of the first device and the second device comprise feedback data chosen from system status and notifications.

12. The method of claim 9, further comprising at least one of the first device and the second device performing designated functions using data chosen from the predefined data, and data provided in the data packets.

13. The method of claim 9, further comprising at least one of the first device and the second device transmitting a message to a peer device in response to one or more of the data packets.

* * * * *